US010617451B2

(12) United States Patent
Sanders et al.

(10) Patent No.: US 10,617,451 B2
(45) Date of Patent: Apr. 14, 2020

(54) BONE FIXATION APPARATUS WITH FASTENER SECUREMENT MECHANISM AND METHODS OF USE

(71) Applicant: REVIVO MEDICAL, LLC, Loudonville, NY (US)

(72) Inventors: Glenn Patrick Sanders, Sand Lake, NY (US); Eric H. Ledet, Schenectady, NY (US); Gary Mittleman, Loudonville, NY (US)

(73) Assignee: REVIVO MEDICAL, LLC, Loudonville, NY (US)

( * ) Notice: Subject to any disclaimer, the term of this patent is extended or adjusted under 35 U.S.C. 154(b) by 0 days.

(21) Appl. No.: 15/995,876

(22) Filed: Jun. 1, 2018

(65) Prior Publication Data

US 2018/0271564 A1    Sep. 27, 2018

Related U.S. Application Data

(63) Continuation of application No. PCT/US2016/064505, filed on Dec. 1, 2016.

(60) Provisional application No. 62/261,842, filed on Dec. 1, 2015.

(51) Int. Cl.
*A61B 17/80* (2006.01)
*A61B 17/70* (2006.01)

(52) U.S. Cl.
CPC ...... *A61B 17/7059* (2013.01); *A61B 17/8023* (2013.01); *A61B 17/8042* (2013.01)

(58) Field of Classification Search
CPC ............ A61B 17/7059; A61B 17/8023; A61B 17/8042; A61B 17/8033; A61B 17/8047
USPC ...................................... 606/70–71, 279–299
See application file for complete search history.

(56) References Cited

U.S. PATENT DOCUMENTS

| 6,361,537 | B1 |  | 3/2002 | Anderson |  |
|---|---|---|---|---|---|
| 6,406,478 | B1 | * | 6/2002 | Kuo | ............... A61B 17/7059 606/295 |
| 7,175,623 | B2 |  | 2/2007 | Thramann |  |
| 7,303,564 | B2 |  | 12/2007 | Freid |  |
| 7,309,304 | B2 |  | 12/2007 | Stewart |  |
| 7,785,327 | B1 | * | 8/2010 | Navarro | ............ A61B 17/8047 606/289 |

(Continued)

FOREIGN PATENT DOCUMENTS

WO    2008106105    9/2008

OTHER PUBLICATIONS

International Search Report and Written Opinion of the International Searching Authority for PCT/US2016/064505, dated Feb. 21, 2017, 12 pages.

*Primary Examiner* — Jessica Weiss
(74) *Attorney, Agent, or Firm* — Heslin Rothenberg Farley & Mesiti P.C.; Jacquelyn A. Graff, Esq.

(57) ABSTRACT

Bone fixation apparatus and spinal implants are disclosed herein. The spinal implants including a body with a first end and a second end, a first attachment portion at the first end, wherein the first attachment portion includes a first opening with at least one lip, a second attachment portion at the second end, wherein the second attachment portion includes a second opening with at least one lip, and an intermediate portion connecting the first attachment portion and the second attachment portion. Surgical methods for inserting the bone fixation apparatus and spinal implants into a patient are also disclosed.

22 Claims, 17 Drawing Sheets

(56) References Cited

U.S. PATENT DOCUMENTS

| | | |
|---|---|---|
| 7,909,859 B2 | 3/2011 | Mosca |
| 8,211,154 B2 | 7/2012 | Fisher |
| 8,764,808 B2 * | 7/2014 | Gonzalez-Hernandez ............... A61B 17/80 606/280 |
| 8,801,712 B2 | 8/2014 | Felix |
| 8,814,869 B2 | 8/2014 | Freid |
| 8,821,553 B2 | 9/2014 | Kirschman |
| 8,858,603 B1 | 10/2014 | Zufelt |
| 9,107,710 B1 | 8/2015 | Swann |
| 9,107,713 B2 * | 8/2015 | Horan ............... A61B 17/8052 |
| 9,351,768 B2 | 5/2016 | Rinner |
| 2002/0183752 A1 * | 12/2002 | Steiner ............... A61B 17/8014 606/282 |
| 2006/0264946 A1 * | 11/2006 | Young ............... A61B 17/1728 606/915 |
| 2009/0187218 A1 | 7/2009 | Schaffhausen |
| 2009/0318921 A1 * | 12/2009 | White ............... A61B 17/8085 606/70 |
| 2011/0106159 A1 | 5/2011 | Nazeck |
| 2011/0251649 A1 * | 10/2011 | Puekert ............... A61B 17/8038 606/289 |
| 2011/0319894 A1 * | 12/2011 | Gupta ............... F04D 25/0613 606/70 |
| 2012/0277748 A1 * | 11/2012 | Trescony ........... A61B 17/7059 606/70 |
| 2013/0190829 A1 * | 7/2013 | Batsch ............... A61B 17/8014 606/291 |
| 2014/0214092 A1 * | 7/2014 | Wolter ............... A61B 17/8057 606/289 |
| 2014/0257395 A1 * | 9/2014 | Ledet ............... A61B 17/7004 606/257 |
| 2015/0025581 A1 | 1/2015 | Carnes |
| 2015/0245859 A1 | 9/2015 | McMillen |
| 2015/0320454 A1 | 11/2015 | Altarac |
| 2016/0089191 A1 | 3/2016 | Pak |

* cited by examiner

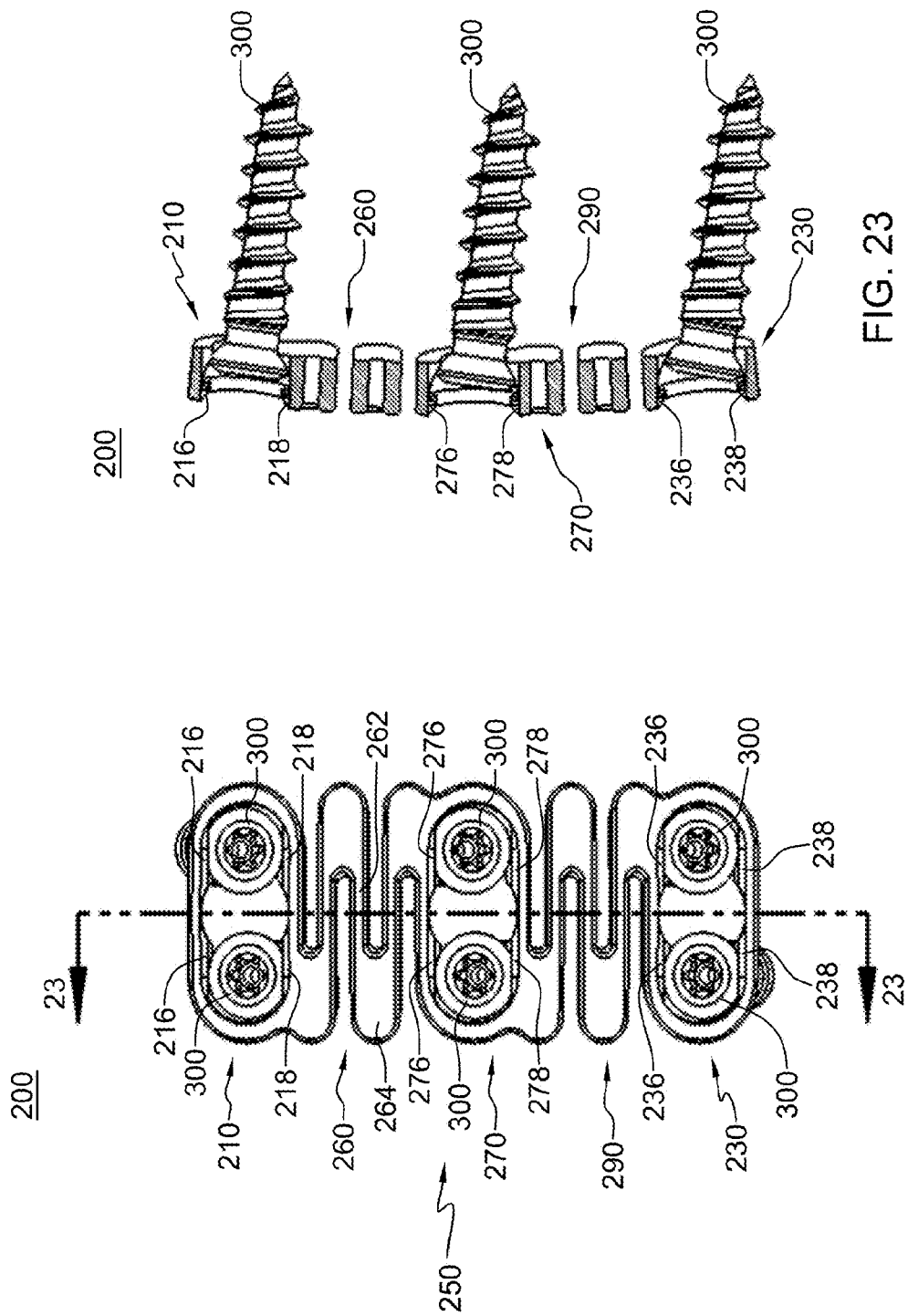

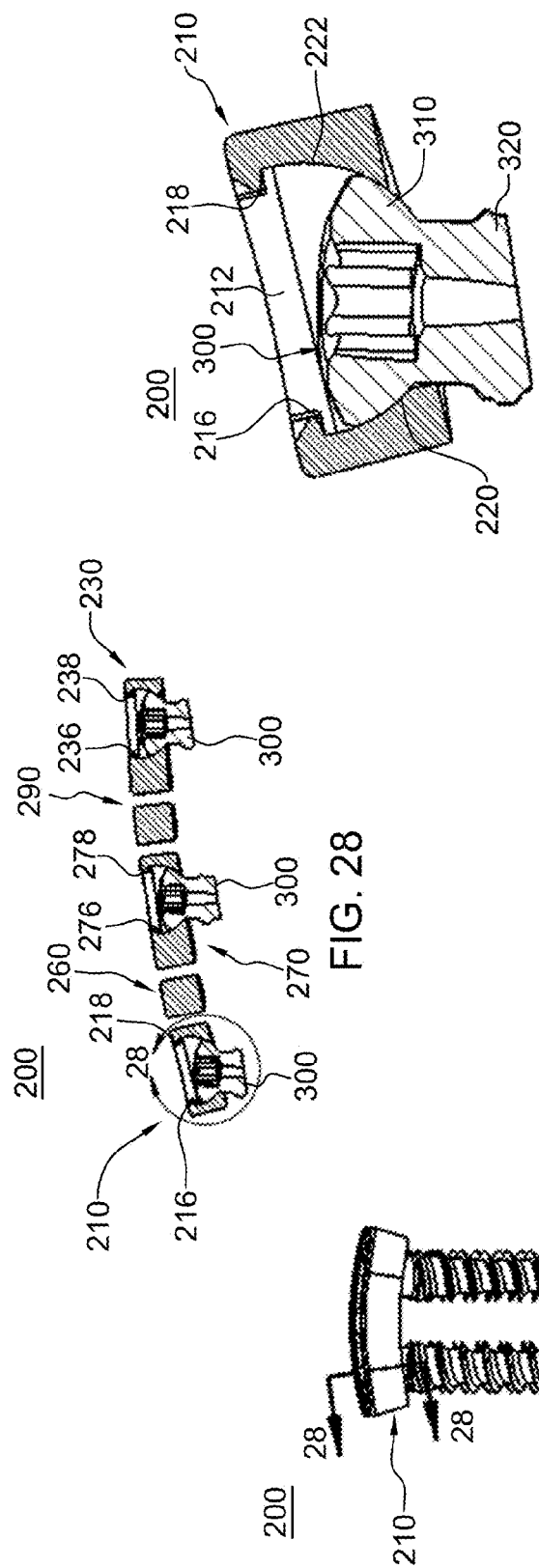

BONE FIXATION APPARATUS WITH FASTENER SECUREMENT MECHANISM AND METHODS OF USE

CROSS REFERENCE TO RELATED APPLICATION

This application is a continuation of PCT Application No. PCT/US2016/064505 filed on Dec. 1, 2016, which claims priority benefit under 35 U.S.C. § 119(e) of U.S. provisional patent application Nos. 62/261,842 filed Dec. 1, 2015, which is incorporated herein by reference in its entirety.

FIELD OF INVENTION

The present invention relates generally to a medical implant for attachment to a patient's vertebrae. More specifically, but not exclusively, the present invention concerns bone fixation devices with anti-backout mechanisms for implantation onto a patient's spine.

BACKGROUND OF THE INVENTION

Many orthopaedic, neurological, or spinal pathologies require fixation of two or more adjacent bone segments using manufactured implants. Such conditions include, but are not limited to: trauma, spinal degeneration, scoliosis, or brain injury. Implants are typically made of metals, polymers, or ceramics, or combinations thereof and may take the form of, but are not limited to: plates, cages, rods, total disc replacements, or combinations thereof. These implants often have apertures to accommodate fasteners. These fasteners most often are screws, but can also take the form of nails, pins, or other forms. Successful fixation requires that the fasteners connectively contact the adjacent bone and do not become disengaged from it. In practice, this disengagement is commonly referred to as "backing out." Thus, these implants often contain mechanisms for preventing backout, commonly called "anti-backout mechanisms." Occasionally, these anti-backout mechanisms also "lock" the fastener to the implant.

SUMMARY OF THE INVENTION

Aspects of the present invention provide a bone fixation apparatus with a fastener securement mechanism for implantation in a patient's spine and methods of using the same. More specifically, methods and apparatuses for stabilizing one or more adjacent bones using a fixation plate with fasteners are disclosed. The apparatus is made of a rigid or elastically deformable body with apertures that facilitate fastener fixation to adjacent bone segments. Some embodiments described herein are methods and apparatuses for preventing the screws from backing out of the plate and other embodiments described herein are methods and apparatuses for securing the screws to the plate.

In one aspect, provided herein is a spinal implant, including a body with a first end and a second end, a first attachment portion at the first end, wherein the first attachment portion includes a first opening with at least one lip, a second attachment portion at the second end, wherein the second attachment portion includes a second opening with at least one lip, and an intermediate portion connecting the first attachment portion and the second attachment portion.

In another aspect, provided here is a method for fusing a spine, including obtaining a spinal implant. The spinal implant including a body with a first end and a second end, a first attachment portion at the first end, wherein the first attachment portion includes a first opening with at least one lip, a second attachment portion at the second end, wherein the second attachment portion includes a second opening with at least one lip, and an intermediate portion connecting the first attachment portion and the second attachment portion. The method may also include aligning the spinal implant over at least two vertebra and inserting a first bone fastener into a first vertebra of a patient through the first opening until the at least one lip engages a top surface of the first bone fastener. The method further includes inserting a second bone fastener into a second vertebra of the patient through the second opening until the at least one lip engages a top surface of the second bone fastener.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 22 is a front view of the bone fixation apparatus of FIG. 21, in accordance with an aspect of the present invention;

FIG. 23 is a cross-sectional view of the bone fixation apparatus of FIG. 22 taken along line 23-23 in FIG. 22, in accordance with an aspect of the present invention;

FIG. 27 is a top view of the bone fixation apparatus of FIG. 14, in accordance with an aspect of the present invention;

FIG. 28 is a cross-sectional view of the bone fixation apparatus of FIG. 14 taken along line 28-28 in FIG. 27, in accordance with an aspect of the present invention;

FIG. 29 is an enlarged view of a portion of the bone fixation apparatus of FIG. 28, in accordance with an aspect of the present invention;

DETAILED DESCRIPTION OF THE PREFERRED EMBODIMENT

Figure 1:
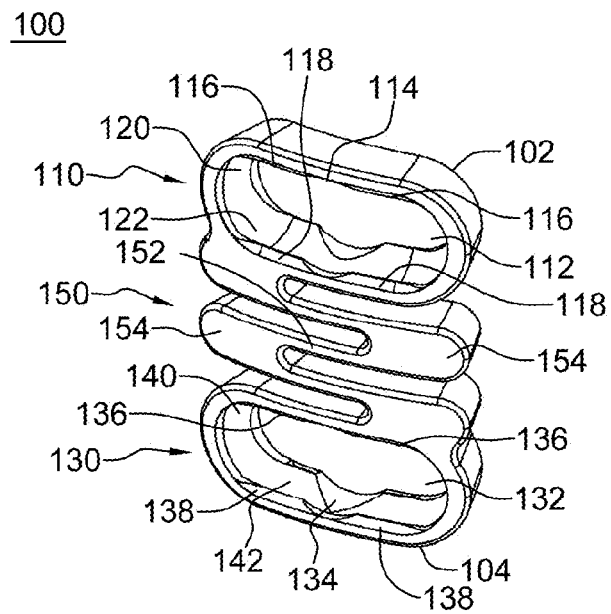
FIG. 1 is a perspective view of one embodiment of a bone fixation apparatus with a fastener securement mechanism, in accordance with an aspect of the present invention.
Figure 2:
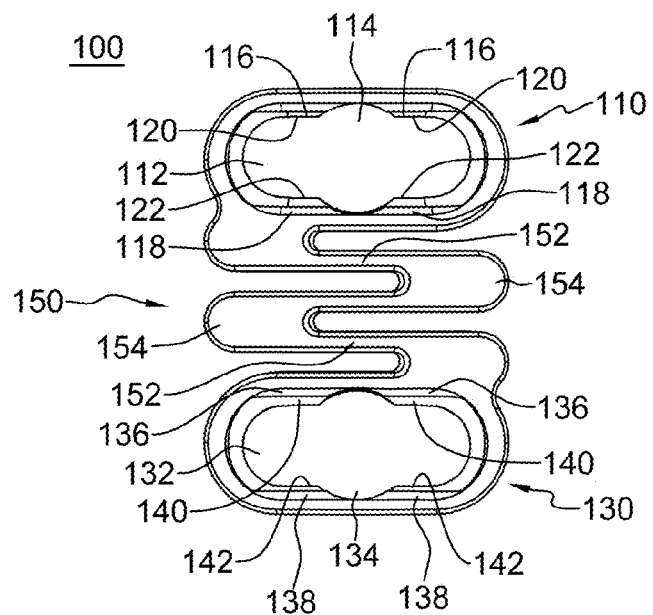
FIG. 2 is a front view of the bone fixation apparatus of FIG. 1, in accordance with an aspect of the present invention.

Generally stated, disclosed herein is a bone fixation device with a fastener securement mechanism. Further, methods of assembling and using the bone fixation device are discussed.

In this detailed description and the following claims, the words proximal, distal, anterior, posterior, medial, lateral, superior, inferior, cephalad, and caudal are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the implant, "posterior" means a direction towards the back side of the implant, "medial" means towards the midline of the implant, "lateral" is a direction towards the sides or away from the midline of the implant, "superior" means a direction above, "inferior" means a direction below another object or structure, "cephalad" means a direction toward the head, and "caudal" means a direction toward the inferior part of the body.

Referring to the drawings, wherein like reference numerals are used to indicate like or analogous components throughout the several views and referring now to FIGS. 1-12 which depicts a bone fixation apparatus, device, implant, or plate 100. The terms "bone fixation system," "bone fixation apparatus," "bone fixation device," "bone fixation implant," "bone fixation plate," "dynamic spinal fixation system," "dynamic spinal fixation apparatus," "dynamic spinal fixation device," "dynamic spinal fixation implant," and "dynamic spinal fixation plate" may be used interchangeably herein to refer to the same mechanism. The bone fixation device 100 is a single level system. The bone fixation device 100 includes a first end 102 and a second end 104. A first attachment portion 110 may be positioned at the first end 102 and a second attachment portion 130 is positioned at the second end 104. An intermediate portion 150 may connect the first attachment portion 110 and the second attachment portion 130.

The first attachment portion 110 and the second attachment portion 130 or platform sections may have a generally closed geometry, for example, a circle, ellipse, square, rectangle, or other closed geometry to facilitate placement of bone fasteners, such as bone screws, nails, staples, wires, pins, and the like. The first attachment portion 110 includes a first opening, aperture, or slot 112 which is oriented in a transverse direction and further includes a relief 114 or a larger aperture creating a "key hole" slot, as shown in FIGS. 1, 2, and 5-8. Likewise, second attachment portion 130 includes a second opening, aperture, or slot 132 which is oriented in a transverse direction and further includes a relief 134 or larger aperture creating a "key hole" slot, as shown in FIGS. 1, 2, and 5-8. As shown, the reliefs 114, 134 may be centered in the first and second openings 112, 132, respectively. It is also contemplated that the reliefs 114, 134 may be positioned anywhere along the first and second openings 112, 132, respectively. In alternative embodiments, the openings 112, 132 could also include additional reliefs allowing for additional bone fasteners to be inserted into the vertebrae before placement of the system 100 onto a patient's spine. In other alternative embodiments, the openings 112, 132 could also be oriented vertically or in any other direction. Multiple openings or tracks 112, 132 in each attachment portion 110, 130 may also be included in alternative embodiments.

As shown in FIGS. 9-12, the first opening 112 may include at least one first lip, brim, retention edge, or rim 116 and at least one second lip, brim, retention edge, or rim 118. The lips 116, 118 may be made of various shapes and various geometries. In one embodiment, the lips 116, 118 may be positioned on, for example, one side of the aperture, such as, the superior or inferior side of the slot 112, and extend or overhang into the slot 112. In another embodiment, the lips 116, 118 may be positioned on, for example, more than one side of the slot 112, such as, both the superior and inferior sides, and extend or overhang into the slot 112. In still another embodiment, the lips 116, 118 may be, for example, continuous around all sides of the slot 112 and extend or overhang into the slot 112. The continuous lip 116, 118 may extend from the superior side of the slot 112, adjacent to the relief 114 to the lateral side and continue to the inferior side. The lips 116, 118 may be positioned near the anterior side of the implant 100. The lips 116, 118 may be an integrated feature on a monolithic implant 100. The lips 116, 118 may be made of a suitable biocompatible material, such as, a metal, polymer, ceramic, composite, or another material that allows for some degree of elastic deformation and plastic deformation.

Figure 10:
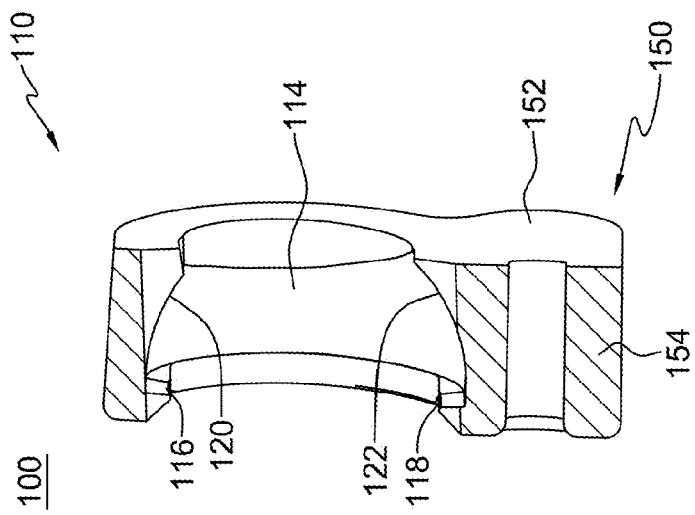
FIG. 10 is an enlarged view of a portion of FIG. 9, in accordance with an aspect of the present invention.
Figure 12:
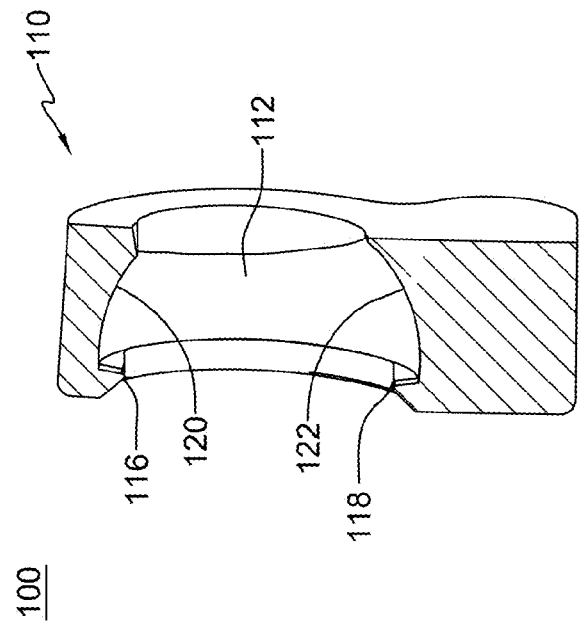
FIG. 12 is an enlarged view of a portion of FIG. 11, in accordance with an aspect of the present invention.

The first opening 112 may also include a first interior surface 120 and a second interior surface 122, as shown in FIGS. 10 and 12. The interior surfaces 120, 122 extend from under the lips 116, 118 to the posterior surface. The interior surfaces 120, 122 may be curved or angled in an anterior to posterior direction to correspond to the bottom surface of a fastener head (not shown). The curvature of the interior surfaces 120, 122 enables the fasteners to be inserted into the patient's bone at varying angles. The relief 114 is inset into the slot 112 and may include interior surfaces 120, 122 that extend from the anterior surface to the posterior surface of the implant 100. The interior surfaces 120, 122 of the relief 114 may be curved or angled in an anterior-posterior direction to correspond to the bottom surface of a fastener head (not shown).

With continued reference to FIGS. 9-12, the second opening 132 may include may include at least one first lip, brim, retention edge, or rim 136 and at least one second lip, brim, retention edge, or rim 138. The lips 136, 138 may be made of various shapes and various geometries. In one embodiment, the lips 136, 138 may be positioned on, for example, one side of the aperture, such as, the superior or inferior side of the slot 132, and extend or overhang into the slot 132. In another embodiment, the lips 136, 138 may be positioned on, for example, more than one side of the slot 132, such as, both the superior and inferior sides, and extend or overhang into the slot 132. In still another embodiment, the lips 136, 138 may be, for example, continuous around all sides of the slot 132 and extend or overhang into the slot 132. The lips 136, 138 may be positioned near the anterior side of the implant 100. The lips 136, 138 may be an integrated feature on a monolithic implant 100. The lips 136, 138 may be made of a suitable biocompatible material, such as, a metal, polymer, ceramic, composite, or another material that allows for some degree of elastic deformation and plastic deformation.

Figure 9:
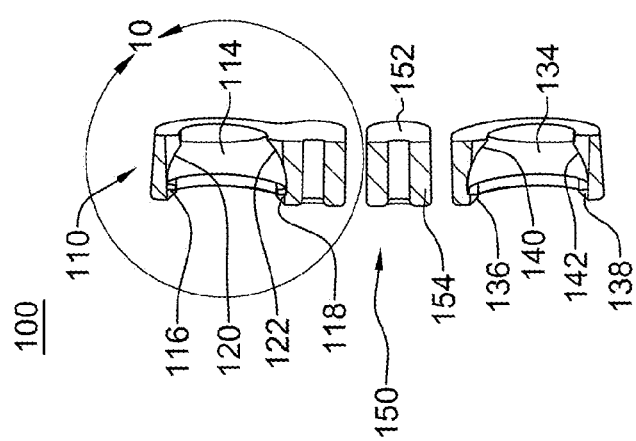
FIG. 9 is a cross-sectional view of the plate of FIG. 1 taken along line 9-9 in FIG. 7, in accordance with an aspect of the present invention.
Figure 11:
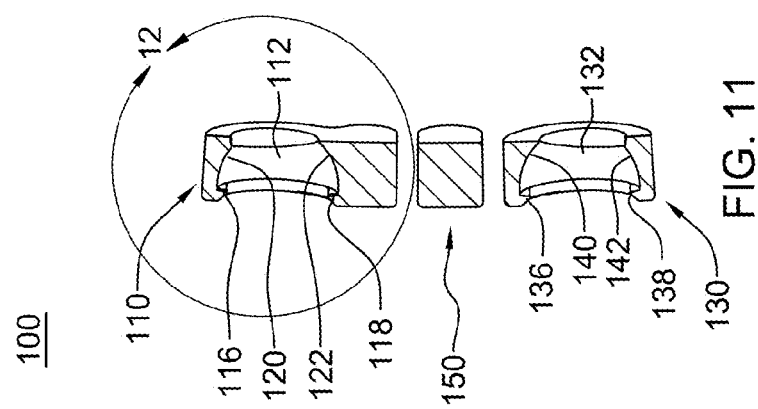
FIG. 11 is a cross-sectional view of the plate of FIG. 1 taken along line 11-11 in FIG. 8, in accordance with an aspect of the present invention.

The second opening 132 may also include a first interior surface 140 and a second interior surface 142, as shown in FIGS. 9 and 11. The interior surfaces 140, 142 extend from under the lips 136, 138 to the posterior surface. The interior surfaces 140, 142 may be curved or angled in an anterior to posterior direction to correspond to the inferior surface of a fastener (not shown). The curvature of the interior surfaces 140, 142 enables the fasteners to be inserted into the patient's bone at varying angles. The relief 134 is inset into the slot 132 and may include interior surfaces 140, 142 that extend from the anterior surface to the posterior surface of the implant 100. The interior surfaces 140, 142 of the relief 134 may be curved or angled in an anterior-posterior direction to correspond to the inferior surface of a fastener (not shown).

The reliefs 114, 134 allow the first attachment portion 110 and second attachment portion 130 to be placed over the bone fastener heads, such as screw heads, that are already fixed to a vertebral body. The bone fasteners could also be pins, wires, nails, or any other method for fixing system 100 to a bone. The first and second openings 112, 132 are smaller than the geometry of the head of the bone fastener and the reliefs 114, 134. Thus, the geometry of the first and second openings 112, 132, respectively, allows the first and second attachment portions 110, 130 to be captured between the bone fastener heads and the underlying vertebra when the system 100 is slid into position between the head of the bone fasteners and the vertebra. Once the system 100 is in a desired position the surgeon may insert additional bone fasteners to secure the system 100 to the patient's spine.

Figure 4:
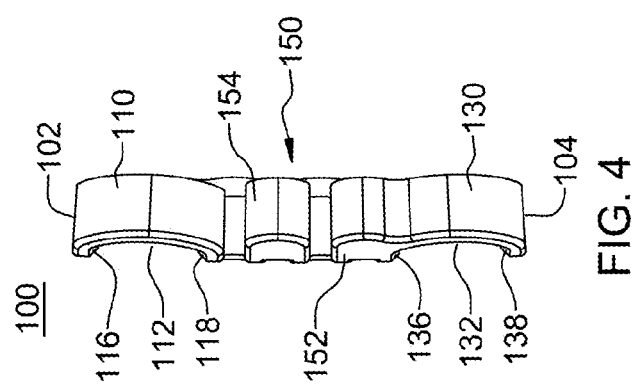
FIG. 4 is a side view of the bone fixation apparatus of FIG. 1, in accordance with an aspect of the present invention.
Figure 3:
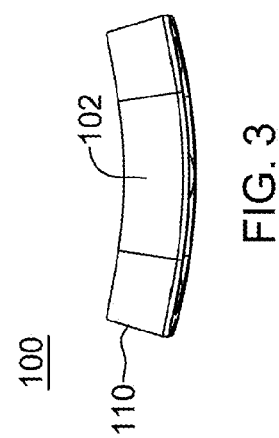
FIG. 3 is a top view of the bone fixation apparatus of FIG. 1, in accordance with an aspect of the present invention.
Figure 6:
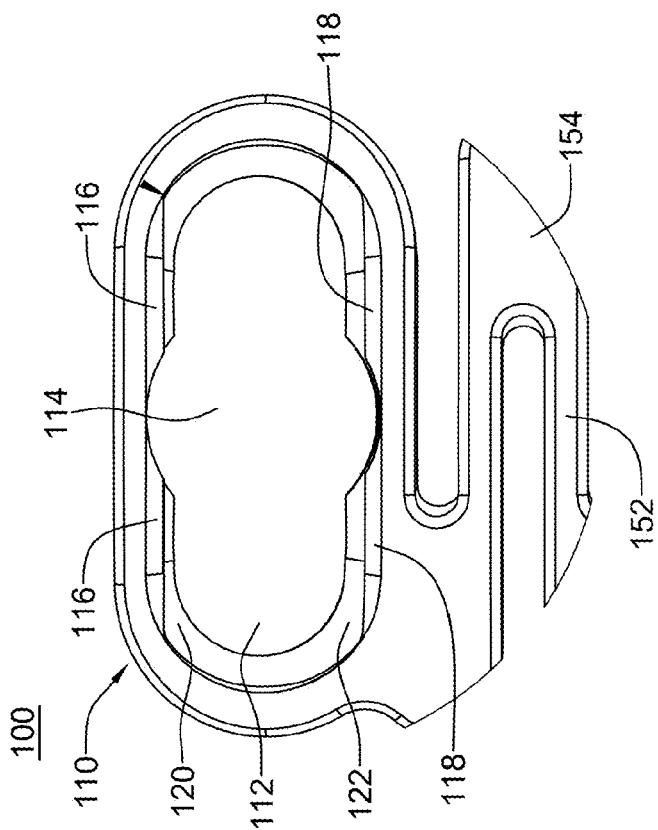
FIG. 6 is an enlarged view of a portion of the bone fixation apparatus of FIG. 5, in accordance with an aspect of the present invention.
Figure 5:
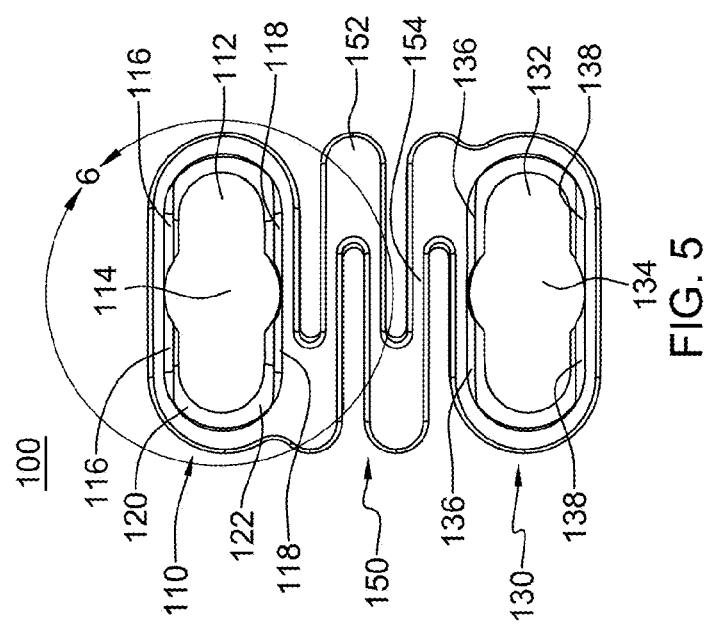
FIG. 5 is a front view of the bone fixation apparatus of FIG. 1, in accordance with an aspect of the present invention.
Figure 7:
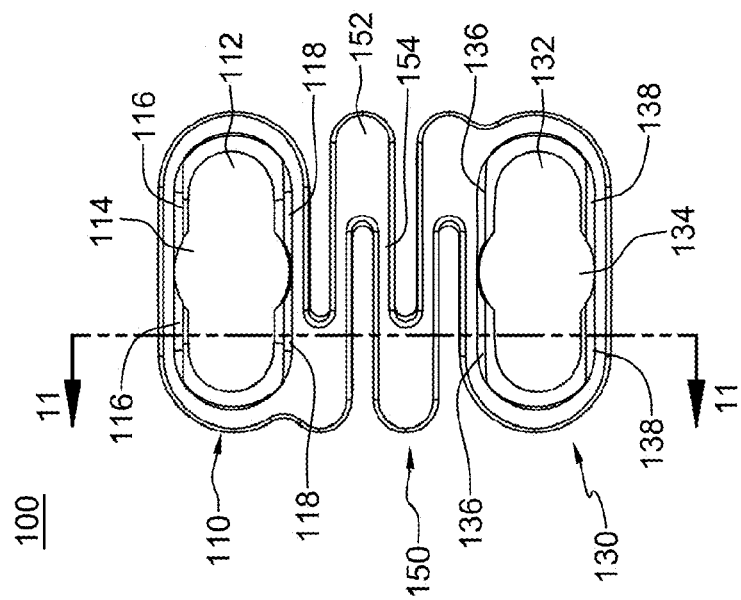
FIG. 7 is a front view of the bone fixation apparatus of FIG. 1, in accordance with an aspect of the present invention.
Figure 8:
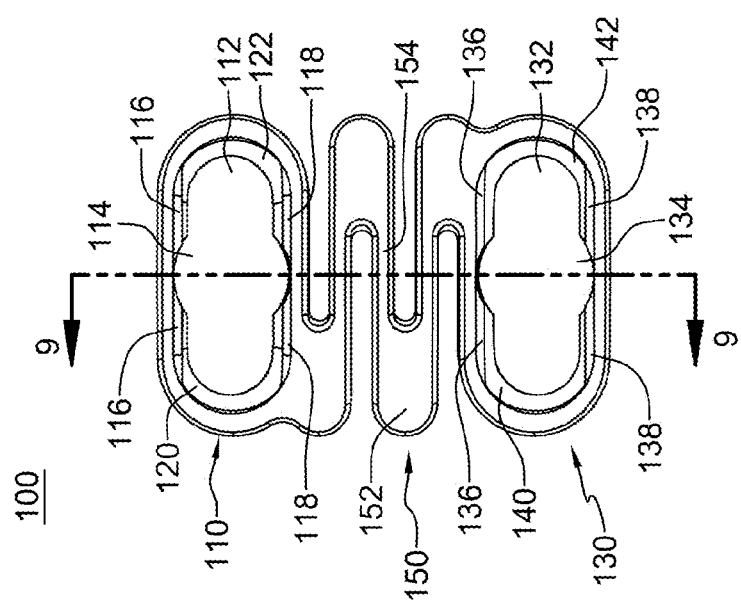
FIG. 8 is a front view of the bone fixation apparatus of FIG. 1, in accordance with an aspect of the present invention.

The intermediate portion 150 may include an elastic mechanism that includes a plurality of straight portions 152 and a plurality of curved portions 154. The straight portions 152 and the curved portions 154 of the elastic mechanism provide open areas to allow for easy spine visualization through the system 100. The elastic mechanism of the intermediate portion 150 may be curvilinear in shape and allow for elastic deformation in any direction when loaded. The deformation of the elastic mechanism or spring-like element is primarily in the axial direction allowing for flexion and extension. The system 100 is designed to be flexible in the superior/inferior direction and more rigid in lateral bending and torsion. Further, the system 100 may be shaped to match the curvature of the spine in the sagittal and transverse planes. As best seen in FIG. 3, the system 100 is curved in the coronal plane to correspond to the shape of the vertebrae. A side view of system 100 is shown in FIG. 4. The system 100 may also be curved in the sagittal plane to correspond to the shape of the spine. The intermediate portion 150 may be made of a non-uniform geometric shape and have a uniform or non-uniform cross-sectional geometry.

Referring now to FIGS. 13-34, another bone fixation system, apparatus, device, implant, or plate 200 is shown. The bone fixation device 200 includes additional attachment portions and either additional or elongated intermediate portions for engaging more than two adjacent vertebrae. For example, and as seen in FIGS. 13-15 and 19-22, the implant 200 may be a two level system for the spine. The system 200 may be shaped to match the curvature of the spine in the sagittal and coronal planes. As best seen in FIGS. 24-27, the system 200 is curved in the coronal plane to correspond to the shape of the vertebrae. A side view of system 200 is shown in FIGS. 19-21 and 23. The system 200 may also be curved in the sagittal plane to correspond to the shape of the spine. The implant 200 includes a first end 202 and a second end 204. The implant 200 includes a first attachment portion 210 positioned at the first end 202 and a second attachment portion 230 positioned at the second end 204. The first and second attachment portions 210, 230 may be of the type described above with reference to FIGS. 1-12, which will not be described again here for brevity sake. The implant 200 may also include an intermediate portion 250 connecting the first attachment portion 210 and the second attachment portion 230. In one embodiment, the intermediate portion 250 may include, for example, a first intermediate member 260, a third attachment portion 270, and a second intermediate member 290. It is also contemplated that the intermediate portion 250 of the plate 200 may include multiple third attachment portions 270 and multiple intermediate members 260, 290 to allow for the plate 200 to be secured to more than two levels of a patient's spine. The intermediate members 260, 290 may be, for example, elastic mechanisms.

As shown in FIGS. 13-15 and 22, the first intermediate member 260 and second intermediate member 290 are of the type described above with reference to intermediate member 150. The first intermediate member 260 and the second intermediate member 290 may each include a single elastic component including a plurality of straight portions 262, 292 and a plurality of curved portions 264, 294. The straight portions 262, 292 and the curved portions 264, 294 provide open areas that allow for easy visualization through the system 200 to a patient's spine. The first intermediate member 260 and the second intermediate member 290 may be curvilinear in shape and allow for elastic deformation in any direction when loaded. The deformation of the elastic mechanism or spring-like element is primarily in the axial direction allowing for flexion and extension. The system 200 is designed to be flexible in the superior/inferior direction and more rigid in lateral bending and torsion. Further, the system 200 may be shaped to match the curvature of the spine in the sagittal and coronal planes, as shown in FIGS. 19-21 and 24-27. The first and second intermediate members 260, 290 may be made of a non-uniform geometric shape and have a uniform or non-uniform cross-sectional geometry.

Figure 13:
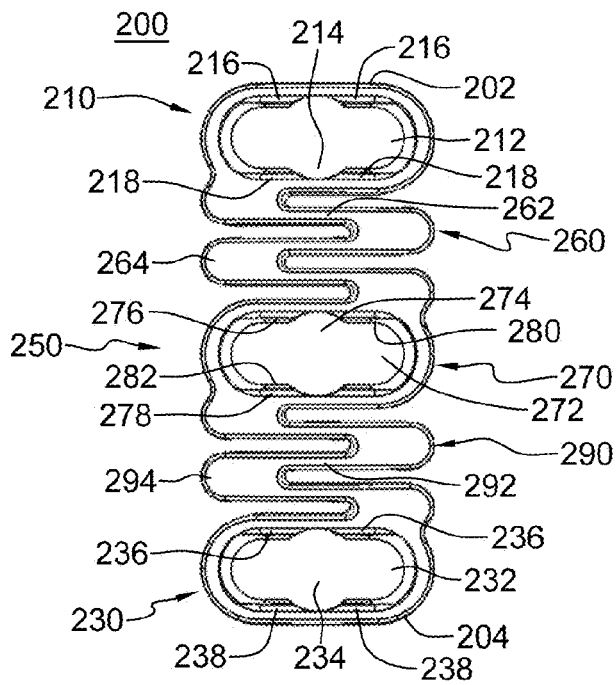
FIG. 13 is a front view of another embodiment of a bone fixation apparatus with a fastener securement mechanism, in accordance with an aspect of the present invention.
Figure 14:
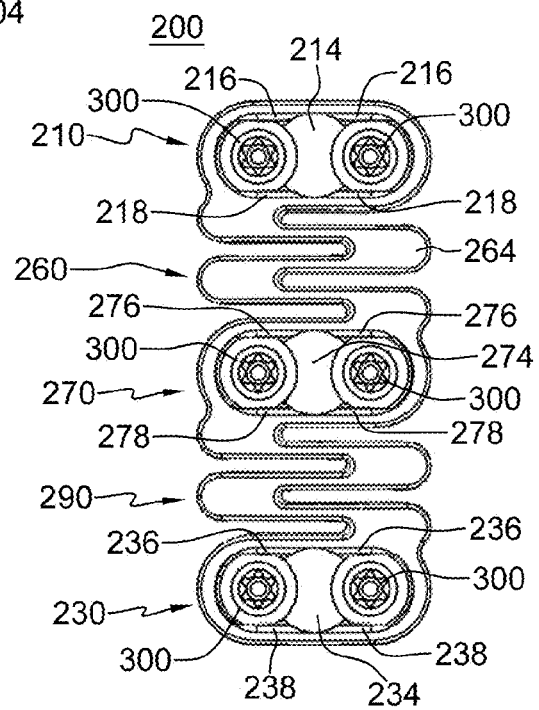
FIG. 14 is a front view of the bone fixation apparatus of FIG. 13 with fasteners inserted, in accordance with an aspect of the present invention.
Figure 15:
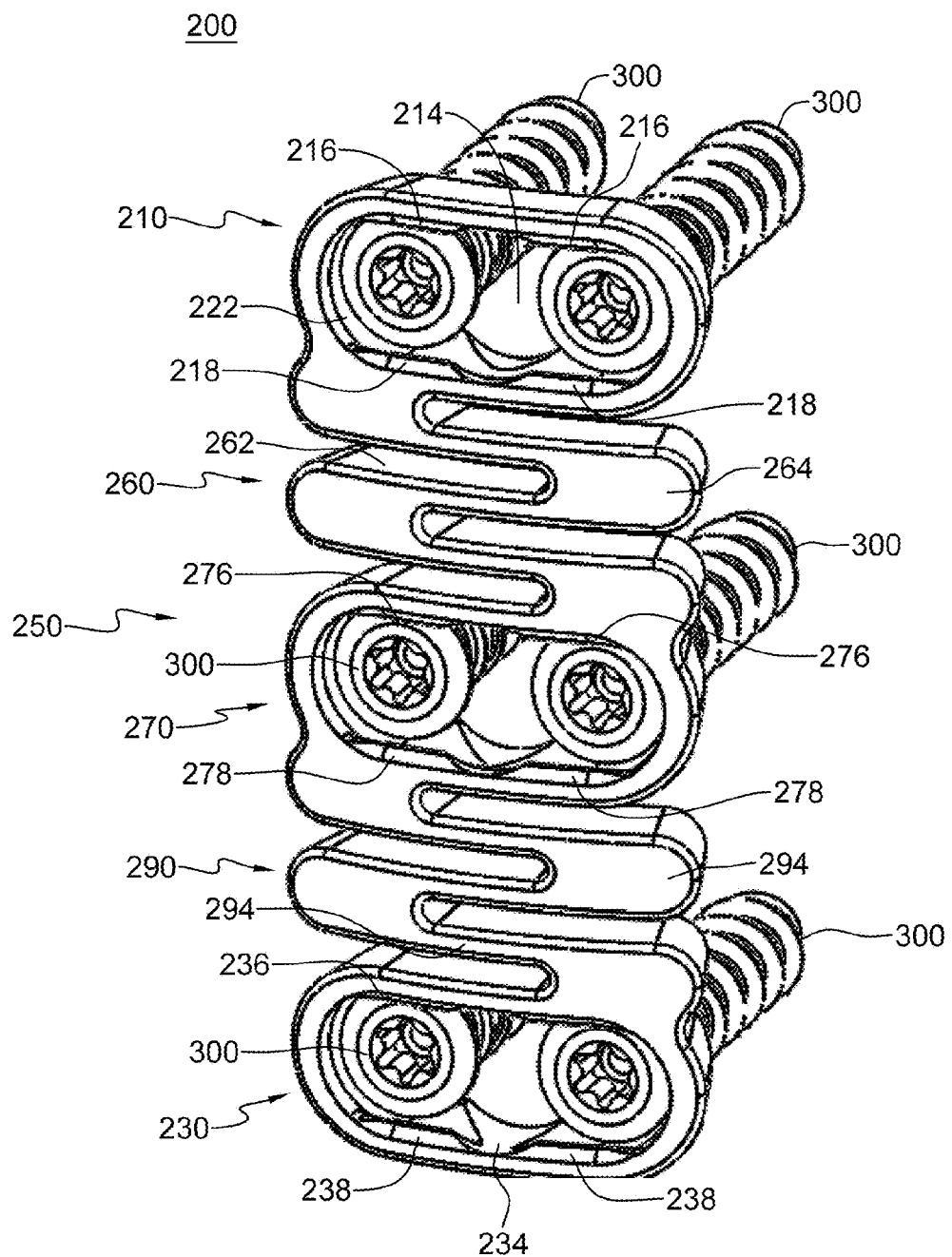
FIG. 15 is a perspective view of the bone fixation apparatus of FIG. 14, in accordance with an aspect of the present invention.

The third attachment portion 270 or platform sections may have a generally closed geometry, for example, a circle, ellipse, square, rectangle, or other closed geometry to facilitate placement of bone fasteners, such as bone screws, nails, staples, wires, pins, and the like. The third attachment portion 270 includes a first opening, aperture, or slot 272 which is oriented in a transverse direction and further includes a relief 274 or a larger aperture creating a "key hole" slot, as shown in FIG. 13. In alternative embodiments, the opening 272 could also include additional reliefs 274 allowing for additional bone fasteners to be inserted into the vertebrae before placement of the system 200 onto a patient's spine. In other alternative embodiments, the openings 272 could also be oriented vertically or in any other direction. Multiple openings or tracks 272 in the third attachment portion 270 may also be included in alternative embodiments.

Figure 16:
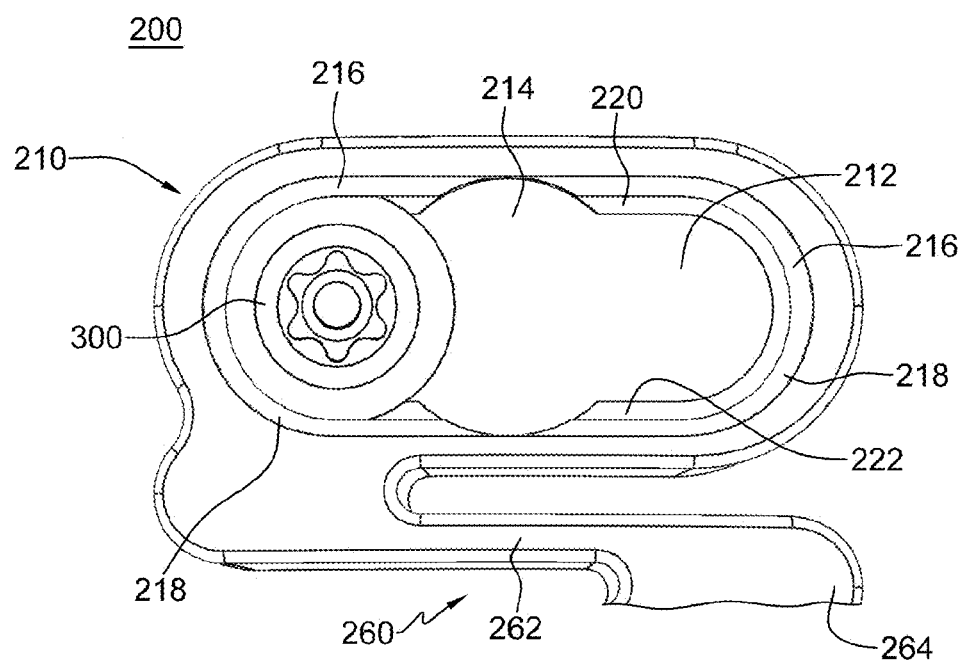
FIG. 16 is a front view of a portion of the bone fixation apparatus of FIG. 13 with one fastener inserted and a fastener securement mechanism positioned on the top, bottom and lateral sides of the opening, in accordance with an aspect of the present invention.
Figure 17:
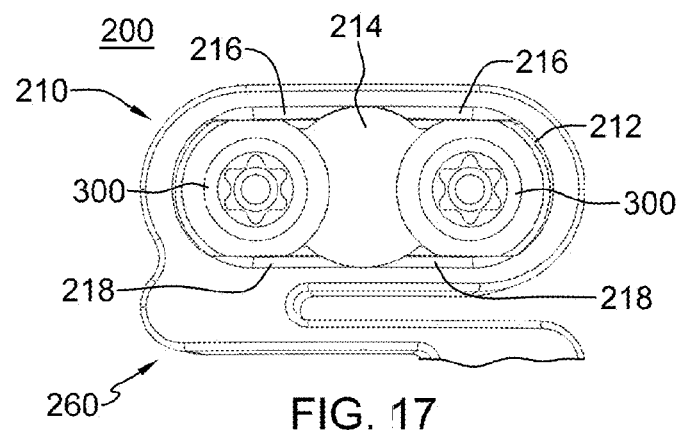
FIG. 17 is a front view of a portion of the bone fixation apparatus of FIG. 13 with two fasteners inserted and a fastener securement mechanism positioned on the top and bottom of the opening, in accordance with an aspect of the present invention.
Figure 18:
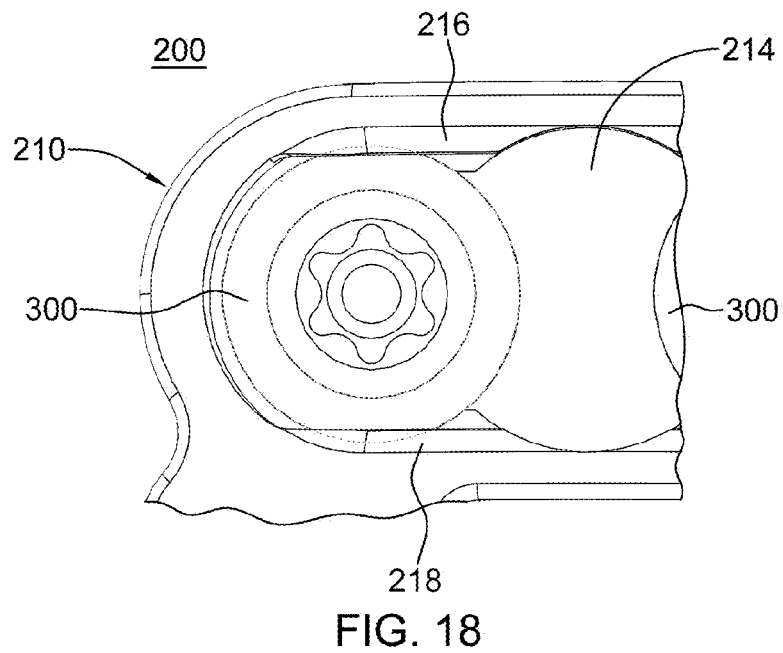
FIG. 18 is an enlarged view of a portion of the bone fixation apparatus of FIG. 17, in accordance with an aspect of the present invention.
Figure 30:
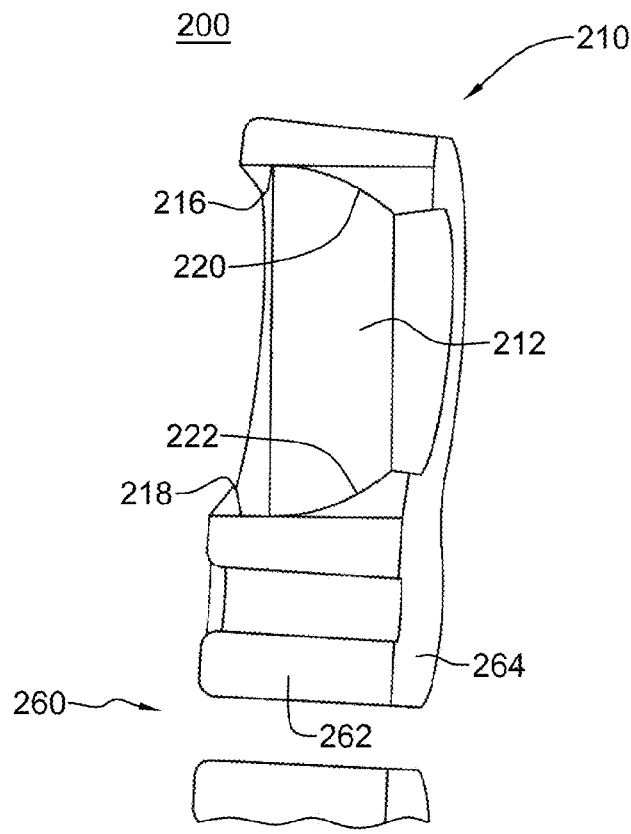
FIG. 30 is a cross-sectional view of a portion of a bone fixation apparatus with two lips, in accordance with an aspect of the present invention.
Figure 31:
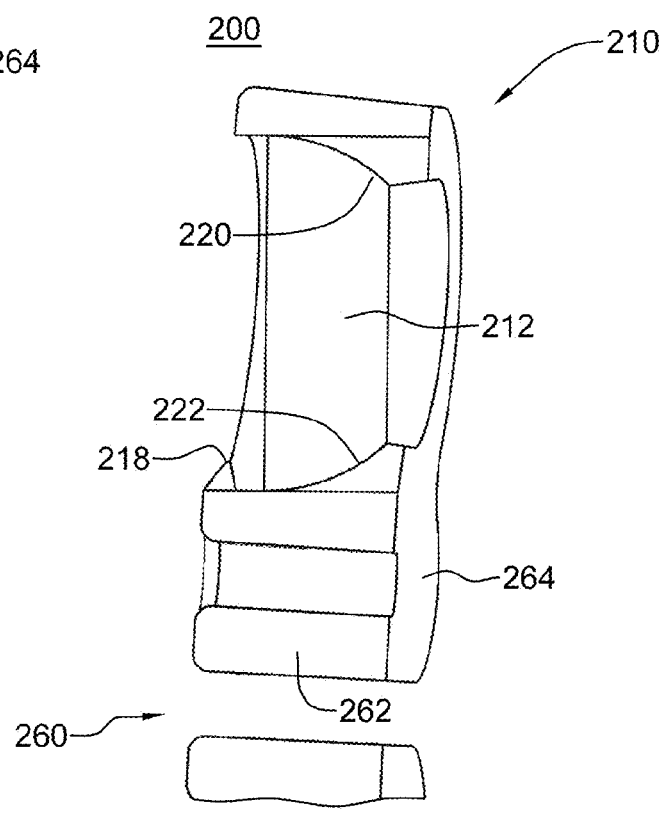
FIG. 31 is a cross-sectional view of a portion of a bone fixation apparatus with one lip, in accordance with an aspect of the present invention.
Figure 34:
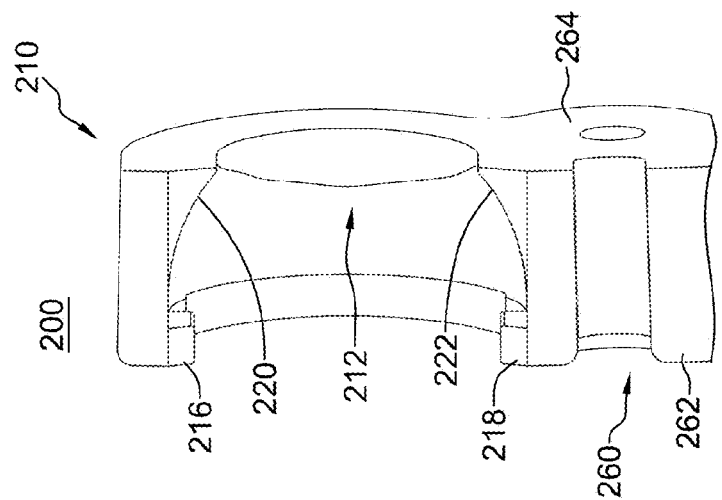
FIG. 34 is a cross-sectional view of a portion of another bone fixation apparatus with two lips, in accordance with an aspect of the present invention.
Figure 33:
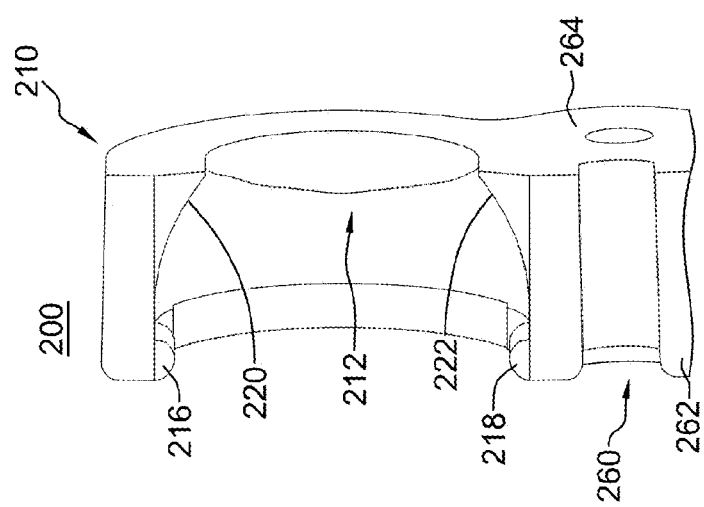
FIG. 33 is a cross-sectional view of a portion of yet another bone fixation apparatus with two lips, in accordance with an aspect of the present invention.
Figure 32:
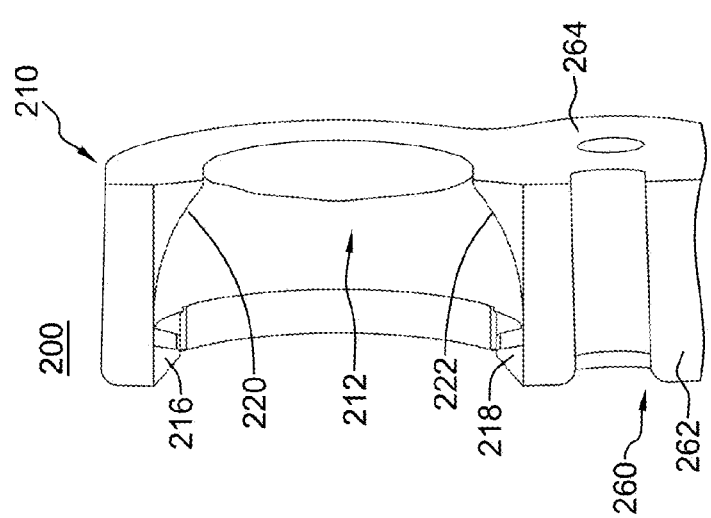
FIG. 32 is a cross-sectional view of a portion of another bone fixation apparatus with two lips, in accordance with an aspect of the present invention.

As shown in FIG. 13, the first opening 272 may include at least one first lip, brim, retention edge, or rim 276 and at least one second lip, brim, retention edge, or rim 278. In one embodiment, as shown in FIG. 31, the lips 216, 218, 236, 238, 276, 278 may be positioned on, for example, one side of the aperture, such as, the superior or inferior side of the slot 212, 232, 272, and extend or overhang into the slot 212, 232, 272. In another embodiment, as shown in FIGS. 17, 18 and 30, the lips 216, 218, 236, 238, 276, 278 may be positioned on, for example, more than one side of the slot 212, 232, 272, such as, both the superior and inferior sides, and extend or overhang into the slot 212, 232, 272. In still another embodiment, as shown in FIG. 16, the lips 216, 218, 236, 238, 276, 278 may be, for example, continuous around all sides of the slot 212, 232, 272 and extend or overhang into the slot 212, 232, 272. The continuous lip 216, 218, 236, 238, 276, 278 may extend from the superior side of the slot 212, 232, 272, adjacent to the relief 214, 234, 274, to the lateral side and continue to the inferior side. As shown in FIG. 16, the lips 216, 218 are positioned on the top, bottom and lateral sides of the slot 212. The lips 216, 218, 236, 238, 276, 278 may be made of various shapes and various geometries. For example, the lips 116, 118, 136, 138, 216, 218, 236, 238, 276, 278 may have a wedge shape as shown in FIG. 32, a hemispherical shape as shown in FIG. 33, a rectangular shape as shown in FIG. 33, or any other like shape to facilitate deformation upon insertion of a fastener and securement of the fastener once inserted into the plate 100, 200. The lips 216, 218, 236, 238, 276, 278 may be positioned near the anterior side of the implant 200. The lips 216, 218, 236, 238, 276, 278 may be an integrated feature on a monolithic implant 200. The lips 216, 218, 236, 238, 276, 278 may be made of a suitable biocompatible material, such as, a metal, polymer, ceramic, composite, or another material that allows for some degree of elastic deformation and plastic deformation.

The third opening 272 may also include a first interior surface 280 and a second interior surface 282, as shown in FIGS. 13 and 23. The interior surfaces 280, 282 extend from under the lips 276, 278 to the posterior surface. The interior surfaces 280, 282 may be curved or angled in an anterior to posterior direction to correspond to the inferior surface of a fastener 300, as shown in FIGS. 23, 28 and 29. The relief 274 is inset into the slot 272 and may include interior surfaces 280, 282 that extend from the anterior surface to the posterior surface of the implant 200. The interior surfaces 280, 282 of the relief 274 may be curved or angled in an anterior-posterior direction to correspond to the inferior surface of a fastener 300. The interior surfaces 280, 282 enable insertion of the fasteners 300 at any angle relative to the plate 200.

The relief 274 allows the third attachment portion 270 to be placed over the bone fastener heads 310, such as screw heads, that are already fixed to a vertebral body. The bone fasteners 300 could also be pins, wires, nails, or any other method for fixing system 200 to a bone. The opening 272 is smaller than the geometry of the head 310 of the bone fastener 300 and the reliefs 274, as shown in FIGS. 14-18. Thus, the geometry of the opening 272 allows the third attachment portion 270 to be captured between the bone fastener heads 310 and the underlying vertebra when the system 200 is slid into position between the head 310 of the bone fasteners 300 and the vertebra. Once the system 200 is in a desired position the surgeon may insert additional bone fasteners 300 to secure the system 200 to the patient's spine.

A surgical method for implanting the device 100, 200 may include preparing the patient for surgery and exposing the surgical site. Next, the desired position of the plate 100, 200 may be determined and at least one first fastener 300 may be inserted into the vertebra. In one embodiment, for example, at least one first fastener 300 may be inserted into at least two adjacent bones. Once the first fasteners 300 are inserted into the bones, the reliefs 114, 134, 214, 234, 274 may be slid over the first fasteners and the plate 100, 200 rotated or translated to align with the patient's spine. As the plate 100, 200 is rotated or translated each first fastener is positioned between one set of lips 116, 118, 136, 138, 216, 218, 236, 238, 276, 278 and one set of corresponding interior surfaces 120, 122, 140, 142, 220, 222, 240, 242, 280, 282. Alternatively, the first fastener may be slid into position in the slot 112, 132, 212, 232, 272 with the fastener head 310 anterior to the plate 100, 200. If the fastener head 310 in positioned anterior to the plate 100, 200, then the fastener 300 may be tightened to secure the plate 100, 200 to the patient's vertebra by positioning the fastener head 310 between the lips 116, 118, 136, 138, 216, 218, 236, 238, 276, 278 and interior surfaces 120, 122, 140, 142, 220, 222, 240, 242, 280, 282.

Then, at least one second set of fasteners 300 may be inserted through the slots 112, 132, 212, 232, 272. During insertion of the at least one second set of fasteners 300 the screw shaft 320 passes by the lips 116, 118, 136, 138, 216, 218, 236, 238, 276, 278. Next, the head 310 of the fastener is passed by the lips 116, 118, 136, 138, 216, 218, 236, 238, 276, 278 and is positioned into the implant 100 between the lips 116, 118, 136, 138, 216, 218, 236, 238, 276, 278 and the interior surfaces 120, 122, 140, 142, 220, 222, 240, 242, 280, 282. The lips 116, 118, 136, 138, 216, 218, 236, 238, 276, 278 extend over the edge of the fasteners 300 to secure the fasteners 300 into the first attachment portion 110, 210, second attachment portion 130, 230, and third attachment portion 270 under normal and extreme physiologic conditions. The lips 116, 118, 136, 138, 216, 218, 236, 238, 276, 278 may have a geometry, specific size and shape, to enable the fasteners 300 to pass during insertion and then prevent the fasteners 300 from backing out past the lips 116, 118, 136, 138, 216, 218, 236, 238, 276, 278 during normal and extreme physiologic conditions. After the implant 100, 200 is secured to the patient's vertebrae the surgical procedure may be completed and the patient closed.

Another surgical method for implanting the device 100, 200 may include preparing the patient for surgery and exposing the surgical site. Next, the desired position of the plate 100, 200 may be determined and at least one first fastener 300 may be inserted through the plate 100, 200 and into the vertebra. In one embodiment, for example, at least one first fastener 300 may be inserted into at least two adjacent bones. During insertion of the at least one first set of fasteners 300, the screw shaft 320 passes by the lips 116, 118, 136, 138, 216, 218, 236, 238, 276, 278. Next, the head 310 of the fastener is passed by the lips 116, 118, 136, 138, 216, 218, 236, 238, 276, 278 and is positioned into the implant 100 between the lips 116, 118, 136, 138, 216, 218, 236, 238, 276, 278 and the interior surfaces 120, 122, 140, 142, 220, 222, 240, 242, 280, 282. The lips 116, 118, 136, 138, 216, 218, 236, 238, 276, 278 extend over the edge of the fasteners 300 to secure the fasteners 300 into the first attachment portion 110, 210, second attachment portion 130, 230, and third attachment portion 270 under normal and extreme physiologic conditions. Alternatively, the first fastener may be slid into position in the slot 112, 132, 212, 232, 272 with the fastener head 310 anterior to the plate 100, 200. If the fastener head 310 in positioned anterior to the plate 100, 200, then the fastener 300 may be tightened to secure the plate 100, 200 to the patient's vertebra by positioning the fastener head 310 between the lips 116, 118, 136, 138, 216, 218, 236, 238, 276, 278 and interior surfaces 120, 122, 140, 142, 220, 222, 240, 242, 280, 282.

Then, at least one second set of fasteners 300 may be inserted through the slots 112, 132, 212, 232, 272 and into the patient's bones to secure the plate 100, 200. Similarly, during insertion of the at least one second set of fasteners 300, the screw shaft 320 pass by the lips 116, 118, 136, 138, 216, 218, 236, 238, 276, 278. Next, the head 310 of the fastener is passed by the lips 116, 118, 136, 138, 216, 218, 236, 238, 276, 278 and is positioned into the implant 100 between the lips 116, 118, 136, 138, 216, 218, 236, 238, 276, 278 and the interior surfaces 120, 122, 140, 142, 220, 222, 240, 242, 280, 282, as shown in FIGS. 14-18 and 22. The lips 116, 118, 136, 138, 216, 218, 236, 238, 276, 278 extend over the edge of the fasteners 300 to secure the fasteners 300 into the first attachment portion 110, 210, second attachment portion 130, 230, and third attachment portion 270 under normal and extreme physiologic conditions. The lips 116, 118, 136, 138, 216, 218, 236, 238, 276, 278 may have a geometry, specific size and shape, to enable the fasteners 300 to pass during insertion and then prevent the fasteners 300 from backing out past the lips 116, 118, 136, 138, 216, 218, 236, 238, 276, 278 during normal and extreme physiologic conditions.

Figure 19:
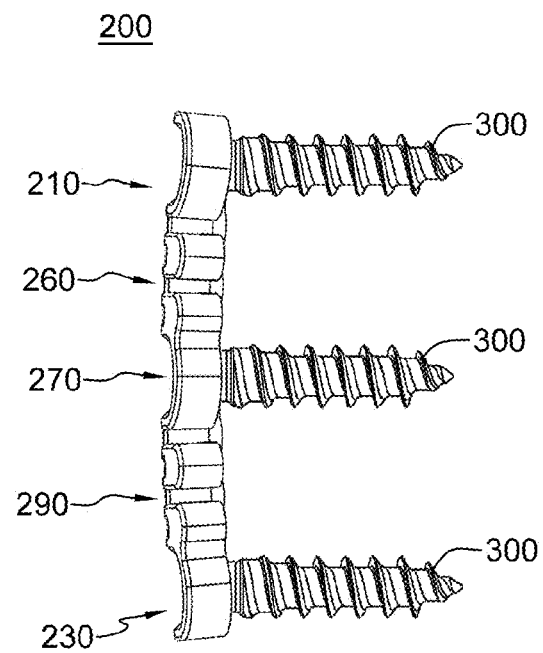
FIG. 19 is a side view of the bone fixation apparatus of FIG. 14 with the fasteners inserted generally perpendicular to the long axis of the plate, in accordance with an aspect of the present invention.
Figure 20:
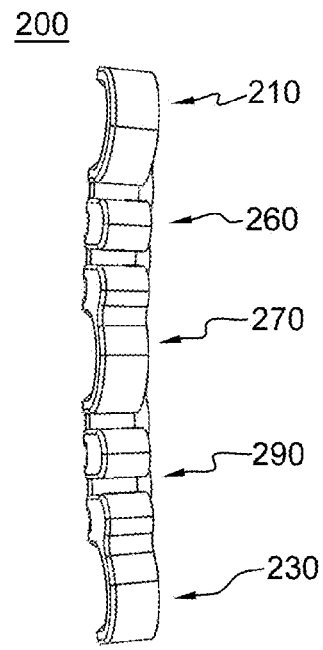
FIG. 20 is a side view of the bone fixation apparatus of FIG. 13, in accordance with an aspect of the present invention.
Figure 21:
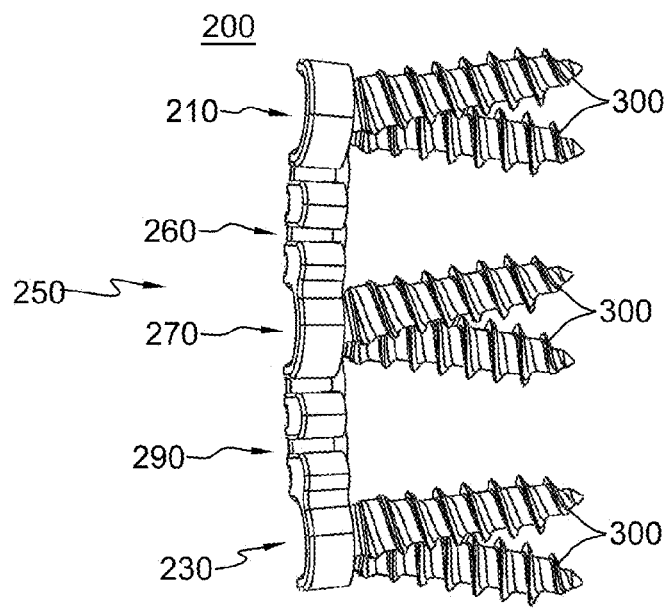
FIG. 21 is a side view of the bone fixation apparatus of FIG. 14 with the fasteners inserted at angles relative to the long axis of the plate, in accordance with an aspect of the present invention.
Figure 24:
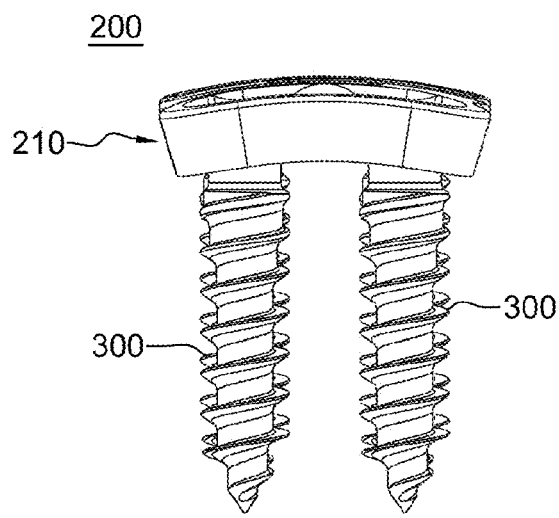
FIG. 24 is a top view of the bone fixation apparatus of FIG. 14, in accordance with an aspect of the present invention.
Figure 25:
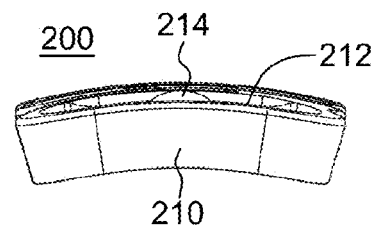
FIG. 25 is a top view of the bone fixation apparatus of FIG. 13, in accordance with an aspect of the present invention.
Figure 26:
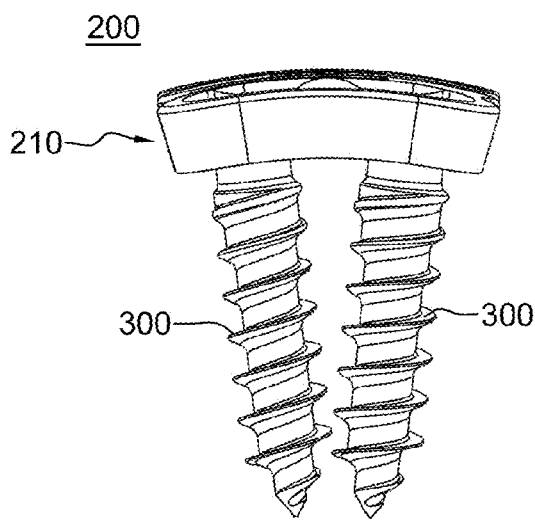
FIG. 26 is a top view of the bone fixation apparatus of FIG. 22, in accordance with an aspect of the present invention.

As shown in FIGS. 19, 24, and 27, the fasteners 300 may be inserted through the plate 100, 200 generally perpendicular to the plate 100, 200. Alternatively, as shown in FIGS. 21, 23, 24, and 26-29, the fasteners 300 may be inserted through the plate 100, 200 at an angle with respect to the plate 100, 200.

Figure 35:
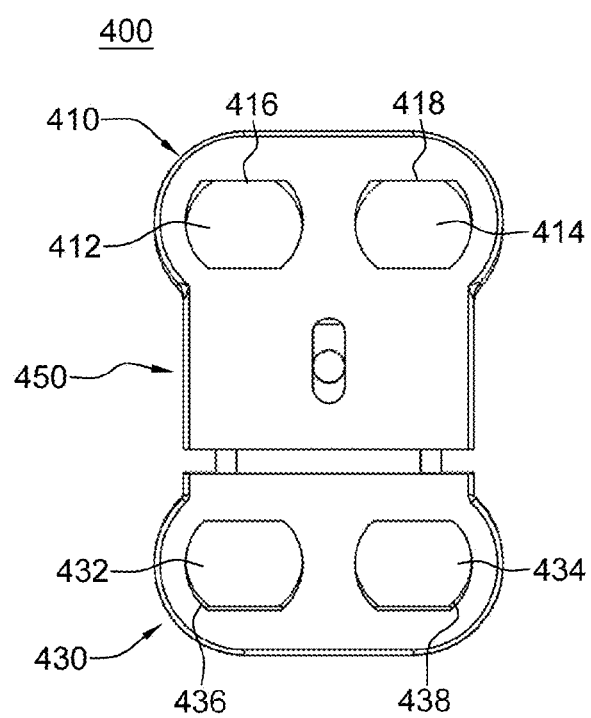
FIG. 35 is a front view of another embodiment of a bone fixation apparatus with attachment portions including retention mechanisms, in accordance with an aspect of the present invention.

Referring now to FIG. 35, another bone fixation system, apparatus, device, implant, or plate 400 is shown. The plate 400 contains at least two attachment portions 410, 430 or rigid platform-like sections which are used to secure the plate 400 to a patient's vertebrae. The attachment portions 410, 430 are generally more rigid than the rest of the plate 400 to facilitate bone fastener fixation to the bony vertebral bodies by allowing bone fasteners (not shown), such as screws, nails, staples, wires, pins, and the like, to pass through the plate 400 at the attachment portion or portions 410, 430. The implant 400 allows for adjustment in length of the intermediate portion 450 along the long axis of the implant 400.

The plate 400 is a multi-component implant. The plate 400 includes a first attachment portion 410 including a first opening 412 and a second opening 414, a second attachment portion 430 including a first opening 432 and a second opening 434, and an intermediate portion 450. The first opening 412 may include a lip, brim, retention edge, or rim 416 positioned around at least a portion of the opening 412. The lip 416 extends into the opening 412. The second opening 414 may include a lip, brim, retention edge, or rim 418 positioned around at least a portion of the opening 414. The lip 418 extends into the opening 414. The first opening 432 may include a lip, brim, retention edge, or rim 436 positioned around at least a portion of the opening 432. The lip 436 extends into the opening 432. The second opening 434 may include a lip, brim, retention edge, or rim 438 positioned around at least a portion of the opening 434. The lip 438 extends into the opening 434. The lips 416, 418, 436, 438 may be an integrated feature on the implant 400. The lips 416, 418, 436, 438 may be made of a suitable biocompatible material, such as, a metal, polymer, ceramic, composite, or another material that allows for some degree of elastic deformation and plastic deformation.

In all embodiments described herein, the implants 100, 200, 400 may be, for example, an elastic fixation plate, a rigid plate, a dynamic plate, a rod, a spinal fusion cage, or a total disc replacement. In all embodiments, the plate 100, 200, 400 contains apertures to accommodate screws. One skilled in the art recognizes that the apertures may accommodate other forms of fasteners such as nails, pins, etc. The lips 116, 118, 136, 138, 216, 218, 236, 238, 276, 278, 416, 418, 436, 438, as described in greater detail above and which will not be described again here for brevity sake, may be monolithic with the apertures of the elastic fixation plates, rigid plates, dynamic plates, rods, spinal fusion cages, total disc replacements, and the like.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An implant, comprising:
    a body with a first end, a second end, an upper surface, a lower bone contacting surface, a first lateral side and a second lateral side;
    a first attachment portion at the first end, wherein the first attachment portion includes a first opening extending from the upper surface to the lower bone contacting surface, and wherein the first opening comprises:
        at least one first lip, wherein the at least one first lip comprises:
            a first lip portion coupled to a first side of the first opening; and
            a second lip portion coupled to a second side of the first opening;
            wherein the at least one first lip extends into the first opening from the upper surface, and wherein the first lip portion of the at least one first lip is spaced apart from the second lip portion of the at least one first lip;
        a first interior surface extending from a portion of the first attachment portion positioned adjacent to the first lip portion of the at least one first lip to the lower bone contacting surface of the body, and wherein at least a portion of the at least one first lip extends into the first opening from an anterior portion of the first interior surface; and
        a second interior surface extending from a portion of the first attachment portion positioned adjacent to the second lip portion of the at least one first lip to the lower bone contacting surface of the body, and wherein at least a portion of the at least one first lip extends into the first opening from an anterior portion of the second interior surface; and
    a second attachment portion at the second end, wherein the second attachment portion includes a second opening extending from the upper surface to the lower bone contacting surface, and wherein the second opening comprises:
        at least one second lip, wherein the at least one second lip comprises:
            a first lip portion coupled to a first side of the second opening; and
            a second lip portion coupled to a second side of the second opening;
            wherein the at least one second lip extends into the second opening from the upper surface, and wherein the first lip portion of the at least one second lip is spaced apart from the second lip portion of the at least one second lip;
        a first interior surface extending from a portion of the second attachment portion positioned adjacent to the first lip portion of the at least one second lip to the lower bone contacting surface of the body, and wherein at least a portion of the at least one second lip extends into the second opening from an anterior portion of the first interior surface; and
        a second interior surface extending from a portion of the second attachment portion positioned adjacent to the second lip portion of the at least one second lip to the lower bone contacting surface of the body, and wherein at least a portion of the at least one second lip extends into the second opening from an anterior portion of the second interior surface;
    and
    an intermediate portion connecting the first attachment portion and the second attachment portion.

2. The implant of claim 1, wherein the first lip portion of the at least one first lip comprises:
    a transition point;
    a top surface extending from a top surface of the body to the transition point at an angle; and
    a bottom surface extending from the transition point to a point of contact with the first interior surface.

3. The implant of claim 1, wherein the first opening extends between the first lateral side and the second lateral side, and wherein the second opening extends between the first lateral side and the second lateral side.

4. The implant of claim 1, wherein the at least one first lip further comprises:
    a third lip portion positioned on at least one lateral side of the first opening and connecting the first lip portion of the first opening and the second lip portion of the first opening; and
    wherein the at least one second lip further comprises:
        a third lip portion positioned on at least one lateral side of the second opening and connecting the first lip portion of the second opening and the second lip portion of the second opening.

5. The implant of claim 1, wherein the first interior surface is curved, wherein the second interior surface is curved, wherein the at least one first lip of the first attachment portion is monolithic with the body, and wherein the at least one second lip of the second attachment portion is monolithic with the body.

6. The implant of claim 1, wherein the first attachment portion further comprises:
a first relief positioned within the first opening, wherein the first relief has a height larger than a height of the first opening, and wherein the first relief is positioned in a center of the first opening between the first lateral side and the second lateral side;
wherein the second attachment portion further comprises:
a second relief positioned within the second opening, wherein the second relief has a height larger than a height of the second opening, and wherein the second relief is positioned in a center of the second opening between the first lateral side and the second lateral side.

7. The implant of claim 1, wherein the intermediate portion comprises:
a third attachment portion with at least one third opening;
a first intermediate member connecting the first attachment portion and the third attachment portion; and
a second intermediate member connecting the third attachment portion and the second attachment portion.

8. The implant of claim 7, wherein the third opening comprises:
at least one third lip, the at least one third lip being monolithic with the body, wherein the at least one third lip comprises:
a first lip portion positioned on a first side of the third opening; and
a second lip portion positioned on a second side of the third opening.

9. The implant of claim 8, wherein the at least one third lip further comprises:
a third lip portion positioned on at least one lateral side of the third opening and connecting the first lip portion of the third opening and the second lip portion of the third opening.

10. The implant of claim 1, further comprising:
at least one first fastener with a head portion positioned below the at least one first lip of the first attachment portion;
at least one second fastener with a head portion positioned below the at least one second lip of the second attachment portion; and
wherein a shaft portion of at least one of the at least one first fastener and the at least one second fastener is angled relative to a long axis of the body.

11. The implant of claim 1, wherein the at least one first lip has a wedge shape and wherein the at least one second lip has a wedge shape.

12. An implant, comprising:
a body with a first end, a second end, an upper surface, a lower bone contacting surface, a first lateral side and a second lateral side;
a first attachment portion at the first end, wherein the first attachment portion includes a first opening extending from the upper surface to the lower bone contacting surface, wherein the first opening has a first width and a first height, wherein the first width is larger than the first height, and wherein the first opening comprises:
at least one first lip, wherein the at least one first lip comprises:
a first lip portion positioned on a first side of the first opening; and
a second lip portion positioned on a second side of the first opening;
wherein the at least one first lip extends into the first opening, and wherein the first lip portion of the at least one first lip is separate from and spaced apart from the second lip portion of the at least one first lip;
a first interior surface extending from a portion of the first attachment portion positioned adjacent to the at least one first lip to the lower bone contacting surface of the body, and wherein at least a portion of the at least one first lip extends into the first opening from an anterior portion of the first interior surface; and
a second interior surface extending from a portion of the first attachment portion positioned adjacent to the at least one first lip to the lower bone contacting surface of the body, and wherein at least a portion of the at least one first lip extends into the first opening from an anterior portion of the second interior surface; and
a second attachment portion at the second end, wherein the second attachment portion includes a second opening extending from the upper surface to the lower bone contacting surface, wherein the second opening has a second width and a second height, wherein the second width is larger than the second height, and wherein the second opening comprises:
at least one second lip, wherein the at least one second lip comprises:
a first lip portion positioned on a first side of the second opening; and
a second lip portion positioned on a second side of the second opening;
wherein the at least one second lip extends into the second opening, and wherein the first lip portion of the at least one second lip is separate from and spaced apart from the second lip portion of the at least one second lip;
a first interior surface extending from a portion of the second attachment portion positioned adjacent to the at least one second lip to the lower bone contacting surface of the body, and wherein at least a portion of the at least one second lip extends into the second opening from an anterior portion of the first interior surface; and
a second interior surface extending from a portion of the second attachment portion positioned adjacent to the at least one second lip to the lower bone contacting surface of the body, and wherein at least a portion of the at least one second lip extends into the second opening from an anterior portion of the second interior surface;
and
an intermediate portion connecting the first attachment portion and the second attachment portion.

13. The implant of claim 12, wherein the at least one first lip has a curvilinear shape, and wherein the at least one second lip has a curvilinear shape.

14. The implant of claim 13, wherein the first interior surface is curved, wherein the second interior surface is curved, wherein the at least one first lip of the first attachment portion is monolithic with the body, and wherein the at least one second lip of the second attachment portion is monolithic with the body.

15. The implant of claim 12, wherein the first opening extends between the first lateral side and the second lateral side, and wherein the second opening extends between the first lateral side and the second lateral side.

16. The implant of claim 12, wherein the at least one first lip further comprises:

a third lip portion positioned on at least one lateral side of the first opening and connecting the first lip portion of the first opening and the second lip portion of the first opening; and wherein the at least one second lip further comprises:
a third lip portion positioned on at least one lateral side of the second opening and connecting the first lip portion of the second opening and the second lip portion of the second opening.

17. The implant of claim 12, wherein the first attachment portion further comprises:
a first relief positioned within the first opening, wherein the first relief has a height larger than a height of the first opening, and wherein the first relief is positioned in a center of the first opening between the first lateral side and the second lateral side; and wherein the second attachment portion further comprises:
a second relief positioned within the second opening, wherein the second relief has a height larger than a height of the second opening, and wherein the second relief is positioned in a center of the second opening between the first lateral side and the second lateral side.

18. The implant of claim 12, wherein the intermediate portion comprises:
a third attachment portion with at least one third opening;
a first intermediate member connecting the first attachment portion and the third attachment portion;
a second intermediate member connecting the third attachment portion and the second attachment portion.

19. The implant of claim 18, wherein the third opening comprises:
at least one third lip, the at least one third lip being monolithic with the body, and wherein the at least one third lip of the third attachment portion comprises:
a first lip portion positioned on a first side of the third opening; and
a second lip portion positioned on a second side of the third opening.

20. The implant of claim 19, wherein the at least one third lip further comprises:
a third lip portion positioned on at least one lateral side of the third opening and connecting the first lip portion of the third opening and the second lip portion of the third opening.

21. The implant of claim 12, further comprising:
at least one first fastener with a head portion positioned below the at least one first lip of the first attachment portion;
at least one second fastener with a head portion positioned below the at least one second lip of the second attachment portion; and
wherein a shaft portion of at least one of the at least one first fastener and the at least one second fastener is angled relative to a long axis of the body.

22. A surgical method for fusing a spine, comprising:
obtaining an implant according to claim 1;
aligning the implant over at least two vertebra;
inserting a first bone fastener into a first vertebra of a patient through the first opening until the at least one first lip engages a top surface of the first bone fastener; and
inserting a second bone fastener into a second vertebra of the patient through the second opening until the at least one second lip engages a top surface of the second bone fastener.

* * * * *